| United States Patent [19] | [11] Patent Number: 4,612,366 |
| --- | --- |
| Nutt | [45] Date of Patent: Sep. 16, 1986 |

[54] CYCLIC HEXAPEPTIDE SOMATOSTATIN ANALOGS

[75] Inventor: Ruth F. Nutt, Green Lane, Pa.

[73] Assignee: Merck & Co., Inc., Rahway, N.J.

[21] Appl. No.: 745,459

[22] Filed: Jun. 17, 1985

[51] Int. Cl.⁴ .................... C07K 7/26; A61K 37/24
[52] U.S. Cl. ................................. 530/311; 814/806
[58] Field of Search ................ 260/112.5 S; 514/806

[56] References Cited

U.S. PATENT DOCUMENTS 4,235,886 11/1980 Freidinger et al. .......... 260/112.5 S
4,310,518 1/1982 Freidinger et al. .......... 260/112.5 S

*Primary Examiner*—Delbert R. Phillips
*Attorney, Agent, or Firm*—David L. Rose; Michael C. Sudol, Jr.

[57] ABSTRACT

Somatostatin analogs are prepared wherein a cyclic hexapeptide contains a secondary amino acid which replaces seven of the ring amino acids of somatostatin. The cyclic hexapeptides are easier to synthesize, have a longer duration of activity, and many have a greater level of activity than somatostatin. The compounds have the properties of inhibiting the release of glucagon, growth hormone and insulin. Certain of the compounds also are capable of inhibiting the release of gastric acid secretions. The compounds are particularly useful in the treatment of acromegaly, diabetes, diabetic retinopathy and peptic ulcers. These cyclic hexapeptides are prepared by the solid phase method and/or solution synthesis.

12 Claims, No Drawings

CYCLIC HEXAPEPTIDE SOMATOSTATIN ANALOGS

BACKGROUND OF THE INVENTION

Somatostatin is a tetradecapeptide incorporating a cyclic dodecapeptide, having the structure:

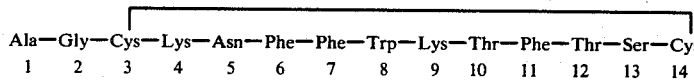

and has the properties of inhibiting the release of growth hormone, inhibiting the release of insulin and glucagon and reducing gastric secretions. Somatostatin itself has a short duration of action because it is inactivated, inter alia, by aminopeptidases and carboxypeptidases present in vivo. This problem of the short duration of action has been partially solved in the prior art by preparing derivatives of somatostatin which have low solubility, thus attaining a slow release on subcutaneous injection. Once dissolved, however, the derivatives are no more stable to inactivation by aminopeptidases and carboxypeptidases than somatostatin itself.

SUMMARY OF THE INVENTION

The present invention provides for cyclic hexapeptides which are derivatives of somatostatin in which, inter alia, seven of the ring amino acids are replaced by a secondary amino acid, and both of the exocyclic amino acids are removed. Further substitution and reaction of the remaining amino acids is also described. The cyclic hexapeptides inhibit the release of glucagon, growth hormones and insulin, and inhibit the release of gastric acid secretions. Specifically the compounds may preferentially inhibit the release of growth hormones without affecting the level of gastric secretions or without affecting the level of gastric secretions, insulin and glucagon, or the compounds may inhibit the release of gastric acid secretions. Thus, the compounds have a more selective biological activity than somatostatin. The cyclic hexapeptide structure of the instant compounds also have a longer duration of activity than somatostatin. As such the instant cyclic hexapeptides are useful for the treatment of acromegaly, diabetes, diabetic retinopathy and peptic ulcers.

Thus, it is an object of the present invention to describe the cyclic hexapeptide somatostatin analogs. A further object is to describe procedures for the preparation of such cyclic hexapeptides. A still further object is to describe the use of such compounds in the treatment of acromegaly, diabetic retinopathy and peptic ulcers. Further objects will become apparent from reading the following description.

DESCRIPTION OF THE INVENTION

The compounds of the instant invention are best realized in the following structural formula:

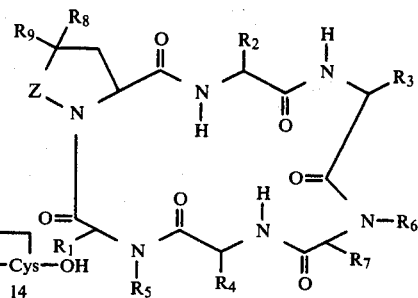

wherein
Z is $(CH_2)_n$; n is 1 or 2;
$R_1$ and $R_2$ are independently loweralkyl, benzyl, naphthylmethyl, indolylmethyl, substituted benzyl where the substitutent may be one or two of loweralkyl, halogen, hydroxy, amino, nitro or loweralkoxy; and loweralkyl substituted with a 5- or 6-membered heterocyclic ring;
$R_3$ is 3-indolylmethyl, naphthylmethyl or substituted 3-indolylmethyl wherein the substituent may be loweralkyl, loweralkoxy, or halogen;
$R_4$ is loweralkyl, hydroxyloweralkyl, benzyl, carboxyloweralkyl, aminoloweralkyl or substituted benzyl wherein the substituent may be loweralkyl, loweralkoxy, hydroxy, halogen, amino or nitro;
$R_5$ and $R_6$ are independently hydrogen or methyl
$R_7$ is aminocyclohexylmethyl, aminomethylbenzyl or

wherein Y is $(CH_2)_m$ and m is 0, 1 or 2 or sulfur such that the sulfur may be in any position along the chain;
$R_8$ and $R_9$ are independently hydrogen, loweralkyl, heteroalkyl wherein the heteroatom is oxygen, sulfur or nitrogen, hydroxy, mercapto and alkanoyl, up to 20 carbon atoms, derivatives of the hydroxy, mercapto and amino groups, and amino, provided that $R_8$ and $R_9$ are not simultaneously hydrogen.

The term "loweralkyl" when used in the instant application is intended to represent those alkyl groups either straight or branched chain, which have from 1-5 carbon atoms. Examples of such alkyl groups are methyl, ethyl, propyl, iso-propyl, butyl, sec-butyl, pentyl and the like.

The term "loweralkoxy" is intended to include those alkoxy groups of from 1-5 carbon atoms, in either a straight or branched chain. Examples of such alkoxy groups are methoxy, ethoxy, propoxy, isopropoxy, butoxy, tert-butoxy, pentoxy and the like.

The term "halogen" or "halo" is intended to include fluorine, chlorine, bromine and iodine.

The term "5- or 6-membered heterocyclic ring" is intended to include those 5- and 6-membered heterocycles with 1- or 2-heteroatoms selected from oxygen, nitrogen and sulfur. Exemplary of such heterocycles is imidazole, furan, thiazole, pyrazole, pyridine and the like.

In the instant compounds there are several assymetric centers which will lead to the existence of optical isomers for such compounds. In the instant invention, for each of the assymetric centers of the various amino acids which make up the instant cyclic hexapeptides, both the D and L configurations are intended to be encompassed.

It will be appreciated by those skilled in the art that when $R_1$ and $R_2$ are benzyl, $R_3$ is indolymethyl, $R_4$ is 1-hydroxyethyl, $R_5$ and $R_6$ are hydrogen, and $R_7$ is $CH_2—CH_2—CH_2CH_2NH_2$, the 7, 8, 9, 10 and 11 amino acids of somatostatin (-Phe-Trp-Lys-Thr-Phe-) are represented, and the secondary amino acid, represented by hydroxy proline when Z is methylene, $R_8$ is hydrogen and $R_9$ is hydroxy, has taken the place of the remainder of the somatostatin amino acids. Thus, using the above definitions of the substituent groups, the following representative cyclic hexapeptide analog of somatostatin is formed in structure I;

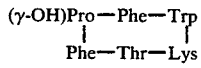

The preferred embodiments of the cyclic hexapeptides of this invention are realized in the foregoing structural formula I wherein Z is $(CH_2)_n$; and n is 1 or 2;
$R_1$ and $R_2$ are as defined above;
$R_3$ is 3-indolylmethyl or substituted indolylmethyl wherein the substituent is methoxy or fluoro;
$R_4$ is methyl, ethyl, hydroxy methyl or hydroxy ethyl;
$R_5$ and $R_6$ are hydrogen;
$R_7$ is $CH_2—CH_2—CH_2CH_2NH_2$;
$R_8$ is hydrogen; and
$R_9$ is hydroxy or acetoxy;
Further preferred embodiments are realized when
Z is methylene;
$R_1$ and $R_2$ are as defined above;
$R_3$ is 3-indolylmethyl;
$R_4$ is hydroxyethyl; and
$R_5$ and $R_6$ are hydrogen;
$R_7$ is $—CH_2CH_2—CH_2CH_2NH_2$;
$R_8$ is hydrogen; and
$R_9$ is hydroxy or acetoxy.

The preferred $R_1$ and $R_2$ groups are loweralkyl, benzyl or substituted benzyl where the substituent is loweralkyl, halogen, hydroxy, amino, nitro or alkoxy.

Included within these preferred compounds are:
Cyclo-(Pro(γ-cis-OH)-Tyr-D-Trp-Lys-Val-Phe)
Cyclo-(Pro(γ-cis-OH)-Tyr-D-Trp-Lys-Thr-Phe)
Cyclo-(Pro(γ-cis-OH)-Phe-D-Trp-Lys-Thr-Phe)
Cyclo-(Pro(γ-cis-OH)-Phe-L-Trp-Lys-Thr-Phe)
Cyclo-(Pro(γ-cis-OH)-Phe-D-Trp-Lys-Thr-p-Cl-Phe)
Cyclo-(Pro(γ-cis-OH)-Phe-D-5-F-Trp-Lys-Thr-Phe)
Cyclo-(Pro(γ-cis-OH)-Phe-L-5-F-Trp-Lys-Thr-Phe)
Cyclo-(Pro(γ-cis-OH)-Phe-D-Trp-Lys-Ser-Phe)
Cyclo-(Pro(γ-cis-OH)-His-D-Trp-Lys-Ser-Phe)
Cyclo-(Pro(γ-cis-OH)-Phe-D-5-F-Trp-AChxAla-Thr-Phe
Cyclo-(Pro(γ-cis-OAc)-Tyr-D-Trp-Lys-Thr-Phe)
Cyclo-(Pro(γ-cis-OAc)-Phe-D-Trp-Lys-Thr-Phe)
Cyclo-(Pro(γ-cis-OAc)-Phe-L-Trp-Lys-Thr-Phe)
Cyclo-(Pro(γ-cis-OAc)-Phe-D-Trp-Lys-Thr-p-Cl-Phe)
Cyclo-(Pro(γ-cis-OAc)-Phe-D-5-F-Trp-Lys-Thr-Phe)
Cyclo-(Pro(γ-cis-OAc)-Phe-L-5-F-Trp-Lys-Thr-Phe)
Cyclo-(Pro(γ-cis-OAc)-Phe-D-Trp-Lys-Ser-Phe)
Cyclo-(Pro(γ-t-OH)-Phe-D-Trp-Lys-Thr-Phe)
Cyclo-(Pro(γ-t-OH)-Phe-L-Trp-Lys-Thr-Phe)
Cyclo-(Pro(γ-t-OAc)-Phe-D-Trp-Lys-Thr-Phe)
Cyclo-(Pro(γ-t-OAc)-Phe-L-Trp-Lys-Thr-Phe)

In the instant application several abbreviated designations are used for the amino acid components, certain preferred protecting groups, reagents and solvents. The meanings of such abbreviated designations are given in Table I.

TABLE I

| Abbreviated Designation | |
|---|---|
| | Amino Acid |
| Lys | L-lysine |
| Phe | L-phenylalanine |
| Trp | L-tryptophan |
| D-Trp | D-tryptophan |
| Thr | L-threonine |
| Tyr | L-tyrosine |
| Val | L-valine |
| Ser | L-serine |
| Asn | L-asparagine |
| Pro | L-proline |
| Cys | L-cysteine |
| AChxAla | aminocyclohexylalanine |
| AmPhe | aminomethylphenylalanine |
| Pro(γ-t-OH) | trans-hydroxyproline-(hydroxyproline) |
| Pro(γ-cis-OH) | cis-hydroxyproline-(allo hydroxyproline) |
| | Protecting Groups |
| INOC | isonicotinyloxycarbonyl |
| BOC | tert-butyloxycarbonyl |
| OMe | methyl ester |
| Bu | tert-butyl |
| CBZ | benzyloxycarbonyl |
| Bzl | benzyl |
| 2-Cl—CBZ | 2-chlorobenzyloxycarbonyl |
| Acm | acetamidomethyl |
| Me | methyl |
| Ac | acetate |
| Ts | tosyl |
| | Activating Groups |
| ONp | p-nitrophenyl ester |
| HSE | N—hydroxysuccinimide ester |
| HBT | 1-hydroxybenzotriazole |
| | Condensing Agents |
| DCCI | dicyclohexylcarbodiimide |
| | Reagents |
| TFA | trifluoroacetic acid |
| TEA | triethylamine |
| DIPEA | diisopropylethylamine |
| DMAP | dimethylaminopyridine |
| | Solvents |
| EPAW | ethyl acetate-pyridine-acetic acid-water |
| BAW | butanol-acetic acid-water |
| CMW | chloroform-methanol-water |
| DMF | dimethylformamide |
| THF | tetrahydrofuran |

In accordance with the present invention, the novel cyclic hexapeptide somatostatin analogs are prepared by cyclizing corresponding linear peptides. The linear peptides are prepared by using the solid phase sequential synthesis technique. Accordingly, the process for preparing the cyclic hexapeptide somatostatin analogs of the present invention comprises (a) preparing a corresponding blocked linear peptide attached to a solid phase resin; (b) selectively deblocking the N-terminal amine group; (c) removing the linear peptide from the resin; (d) treating the linear peptide with a cyclizing agent to obtain the cyclic hexapeptide through the formation of an amide bond; (e) removing any side chain blocking groups.

When the linear peptide is prepared on the resin, it is generally not critical which amino acid is selected to be at the C-terminal position provided only that the sequence of amino acids in the linear peptide corresponds to that in the desired somatostatin analog. Once a linear peptide has been cyclized one can no longer determine which amino acid was at the C-terminus of the linear peptide.

While generally the selection of the first amino acid to start the chain is not critical, since the linear peptide will be cyclized, there may be other factors which may prefer one starting amino acid over another. For example D-Trp can react with t-butyl carbonium ions which are formed when BOC groups are removed. Thus, selection of a reaction sequence which places D-Trp at the N-terminal end of the linear peptide will cause D-Trp to be added last, and thus it will have the least exposure to t-butyl carbonium ions. This type of selection may not always be possible, such as where there are two indole containing moieties in the peptide. However, such reaction sensitivities should be considered when planning a peptide reaction sequence.

The synthesis of the linear peptides by the solid phase technique is conducted in a stepwise manner on chloromethylated resin. The resin is composed of fine beads (20-70 microns in diameter) of a synthetic resin prepared by copolymerization of styrene with 1 to 2 percent divinylbenzene. The benzene rings in the resin are chloromethylated in a Friedel-Crafts reaction with chloromethyl methyl ether and stannic chloride. The Friedel-Crafts reaction is continued until the resin contains 0.5 to 5 mmoles of chlorine per gram of resin.

The amino acid selected to be the C-terminal amino acid of the linear peptide is converted to its amino protected derivative. The carboxyl group of the selected C-terminal amino acid is bound covalently to the insoluble polymeric resin support, as for example, as the carboxylic ester of the resin-bonded benzyl chloride present in chloromethyl-substituted polystyrene-devinylbenzene resin. After the amino protecting group is removed, the amino protected derivative of the next amino acid in the sequence is added along with a coupling agent, such as dicyclohexylcarbodiimide. The amino acid reactant may be employed in the form of a carboxyl-activated amino acid such as the ONp ester, an amino acid azide, and the like. Deprotection and addition of successive amino acids is performed until the desired linear peptide is formed.

The selection of protecting groups is, in part, dictated by particular coupling conditions, in part by the amino acid and peptide components involved in the reaction.

Amino-protecting groups ordinarly employed include those which are well known in the art, for example, urethane protecting substituents such as benzyloxycarbonyl (carbobenzoxy), p-methoxycarbobenzoxy, p-nitrocarbobenzoxy, t-butyloxycarbonyl, and the like. It is preferred to utilize t-butyloxy carbonyl (BOC) for protecting the α-amino group in the amino acids undergoing reaction at the carboxyl end of said amino acid. The BOC protecting group is readily removed following such coupling reaction and prior to the subsequent step by the relatively mild action of acids (i.e. trifluoro acetic acid, or hydrogen chloride in ethyl acetate).

The OH group of Thr and Ser can be protected by the Bzl group and the ε-amino group of Lys can be protected by the INOC group or the 2-chlorobenzyloxycarbonyl (2-Cl-CBZ) group. In the case of Lys, it is preferred to protect the ε-amino group with 2-Cl-CBZ group as this group is removed simultaneously with the Bzl groups by treatment with HF after the linear peptide has been cyclized. The INOC group is not removed by HF and requires an additional treatment with Zn. Neither group is affected by TFA, used for removing BOC protecting groups. After the linear peptide is cyclized, the protective groups, such as 2-Cl-CBZ and Bzl, are removed by treatment with HF.

After the linear peptide has been formed on the solid phase resin, it may be removed from the resin by a variety of methods which are well known in the art. For example the peptide may be cleaved from the resin with hydrazine and thus directly form the peptide hydrazide which may be subsequently cyclized via the azide to the desired cyclic peptide. The hydrazide is converted to the corresponding azide by reaction with a reagent which furnishes nitrous acid in situ. Suitable reagents for this purpose include a lower alkyl nitrite (e.g. t-butyl nitrite, isoamyl nitrite) or an alkali metal nitrite salt (e.g., sodium nitrite, potassium nitrite) in the presence of a strong acid such as hydrochloric, phosphoric, etc. This reaction is carried out in the presence of either water and/or a non-aqueous solvent such as dimethylformamide, tetrahydrofuran, dioxane, chloroform, methylene chloride, etc., at a temperature between about $-40°$ C. and $+20°$ C. Alternatively, the peptide may be removed from the resin by treatment with a lower alcohol such as methanol in the presence of an organic base such as triethylamine, thus resulting in the formation of the corresponding lower alcohol ester of the linear peptide. The resulting ester may be converted to the hydrazide which may then be cyclized, via the azide, to the desired cyclic peptide. The preferred method for cleaving the peptide from the resin in the present invention is the use of hydrazine.

Those compounds wherein $R_8$ and $R_9$ is loweralkanoyloxy are prepared from the compound wherein such group is hydroxy by acylation of such hydroxy group. Generally the loweralkanoyloxy group is not present initially on the amino acid reactant in order to avoid the removal by hydrolysis of such group. The hydroxy on the hydroxy proline amino acid is sufficiently non-reactive such that there is generally no need to protect such group during the preparation of the linear peptide and the cyclization thereof. The best time to prepare the acylated hydroxyproline compound is after the cyclization of the linear peptide and prior to the removal of the protecting groups.

The acylation is carried out in usual acylation media such as the loweralkanoyl anhydride, preferably acetic anhydride and a basic catalyst, such as a tertiary or aromatic amine. Generally trialkyl amines, and pyridine are satisfactory, however, dimethylaminopyridine is preferred. The reaction generally is carried out at about 0° to 50° C. for from 30 minutes to 24 hours, and preferably at room temperature for about 1 hour. In excess of the anhydride or the acylating reagent many used such that no separate solvent is required, however, an inert solvent such as a chlorinated hydrocarbon is generally employed. The product is recovered using known techniques. It is intended that all structural and optical isomers are included in the instant invention and such compounds may be prepared using the structurally or optically pure isomer of the starting amino acid. One particular case, the cis hydroxy proline compound is available as the optically pure starting material cis or allo hydroxy proline. However, this compound is very expensive and it has been discovered that a variation of the above acylation technique will prepare the pure cis hydroxy and alkanoyloxy proline compounds from the corresponding trans compound. Using the cyclized and protected peptide as in the acylation process, the hydroxy of the hydroxy proline is treated with tosylchloride to prepare the tosylate derivative. This reaction is carried out using the same reaction conditions as with the above acylation reaction. The tosylate is then reacted with an acylating cesium reagent such as cesium acetate in a solvent such as N,N-dimethylformamide, at for 25° to 100° C. for 1–30 hours. The reaction inverts the structure at the carbon containing the acyl group as the tosylate is displaced. The reaction produces the cis loweralkanoyl derivative as well as the cis hydroxy compound. The products are separated and isolated using techniques known to those skilled in the art.

As reference Table II will show, one preferred overall procedure for preparing the desired cyclic peptides of the present invention involves the stepwise synthesis of the linear peptide on a solid phase resin. More specifically, in the process for preparing:

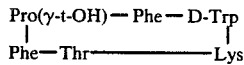

Pro(γ-t-OH)—Phe—D-Trp
|                      |
Phe—Thr———————Lys the carboxyl end of the N-blocked amino acid threonine is bound covalently to an insoluble polymeric resin support as the carboxylic acid ester of the resin-bonded benzyl chloride. The amino group of Thr is protected by the BOC group and the OH of the Thr is protected with a benzyl group. After the attachment of the (BOC)Thr(BZL) is completed on the resin, the protecting group BOC is removed by treatment with TFA in CH$_2$Cl$_2$. The subsequent amino acids are attached, in the form of BOC-amino acid, using DCCI as the condensing agent or an active ester such as ONp. After the desired linear peptide has been prepared, the N-terminal amino group is selectively deblocked and the peptide is removed from the resin by treatment with hydrazine. The resulting linear peptide hydrazide with the N-terminal amino group deblocked having the amino acid sequence.

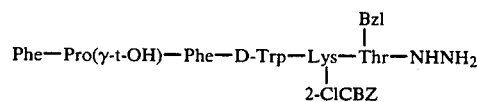

Phe—Pro(γ-t-OH)—Phe—D-Trp—Lys—Thr—NHNH$_2$
                              |
                          2-ClCBZ
                                    Bzl is treated with isoamyl nitrite in acid pH to form the corresponding azide. The azide solution is diluted with solvent and neutralized with an organic base. The linear peptide cyclizes to form:

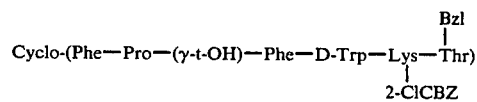

Cyclo-(Phe—Pro—(γ-t-OH)—Phe—D-Trp—Lys—Thr)
                                 |
                             2-ClCBZ
                                       Bzl During the cyclization the "pH" is checked and maintained at neutral by the addition of organic base. The "pH" in organic solvent is determined by the application of an aliquot of the solution to moistened narrow range pH paper.

After the linear peptide is cyclized, the protective groups, 2-Cl-CBZ and OBzl, are removed by treatment with HF in the presence of anisole. The crude cyclic peptide obtained is purified chromatographically, preferably with column chromatography on silica gel. The elution solvent is generally an organic solvent or mixtures thereof which is selected by analyzing aliquots of the material using thin layer chromatography.

TABLE II

Reaction scheme for preparing:

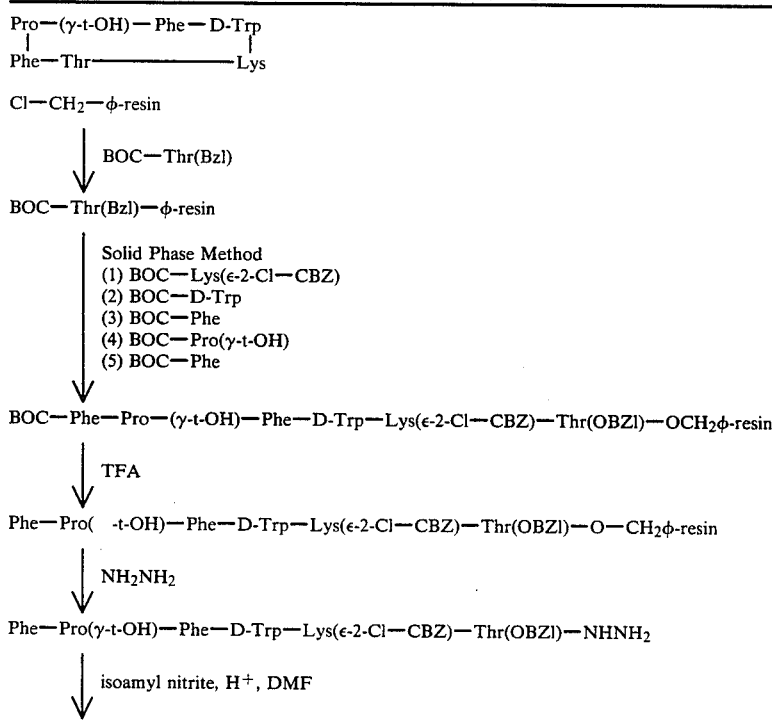

Pro—(γ-t-OH)—Phe—D-Trp
|                      |
Phe—Thr———————Lys

Cl—CH$_2$—φ-resin

↓ BOC—Thr(Bzl)

BOC—Thr(Bzl)—φ-resin

Solid Phase Method
(1) BOC—Lys(ε-2-Cl—CBZ)
(2) BOC—D-Trp
(3) BOC—Phe
(4) BOC—Pro(γ-t-OH)
(5) BOC—Phe BOC—Phe—Pro—(γ-t-OH)—Phe—D-Trp—Lys(ε-2-Cl—CBZ)—Thr(OBZl)—OCH$_2$φ-resin

↓ TFA

Phe—Pro( -t-OH)—Phe—D-Trp—Lys(ε-2-Cl—CBZ)—Thr(OBZl)—O—CH$_2$φ-resin

↓ NH$_2$NH$_2$

Phe—Pro(γ-t-OH)—Phe—D-Trp—Lys(ε-2-Cl—CBZ)—Thr(OBZl)—NHNH$_2$

↓ isoamyl nitrite, H$^+$, DMF

TABLE II-continued

Reaction scheme for preparing:

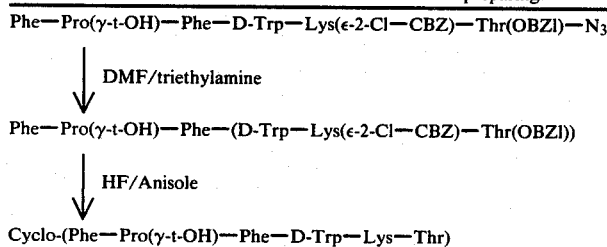

Phe—Pro(γ-t-OH)—Phe—D-Trp—Lys(ε-2-Cl—CBZ)—Thr(OBZl)—N₃

↓ DMF/triethylamine

Phe—Pro(γ-t-OH)—Phe—(D-Trp—Lys(ε-2-Cl—CBZ)—Thr(OBZl))

↓ HF/Anisole

Cyclo-(Phe—Pro(γ-t-OH)—Phe—D-Trp—Lys—Thr)

The following Examples are given to illustrate the methods used to carry out the present invention. It is to be understood that these Examples are given for purposes of illustration and not limitation.

EXAMPLE 1

Preparation of
Phe-Pro(γ-t-OH)-Phe-D-Trp-Lys(ε-2-Cl-CBZ)-Thr(BZl)-OCH$_2$ φ-resin Chloromethyl resin (2% cross-linked Merrifield resin), 862.0 g. (2.37 moles), having 2.75 meq. chlorine/g., and 732.3 g. (2.37 moles, 1 equivalent) of BOC-Thr(Bzl) were added to 4320 ml. of peroxide-free tetrahydrofuran. The mixture was stirred in an oil bath at 80° C. bath temperature for 45 minutes. Triethylamine, 310.0 ml., was added and the reaction mixture stirred at 80° C. bath temperature for 70 hours, cooled to 25° C. and transferred to a stirred solid phase reaction column with 2000 ml. of tetrahydrofuran. After removal of the solvent, the resin was washed using the stirred column with:

3×2000 ml. of tetrahydrofuran
4×5170 ml. of ethanol
1×5170 ml. of acetic acid
3×5170 ml. of water
3×5710 m. of methanol
3×5170 ml. of chloroform The BOC-Thr-(Bzl)-O-CH$_2$φ-resin was dried in vacuo at 25° C. for 16 hours, giving 1203 g. of BOC-Thr(Bzl)-O-CH$_2$ φ-resin containing 1.2 mmole of threonine/g. resin.

BOC-Thr(BZl)-O-CH$_2$ φ-resin (2.13 g.; 2.0 mmole) was carried through the procedures in Tables III and IV using 2 deblockings (2 minutes and 25 minutes) with 25% TFA in methylene chloride and 2.5 equivalents of BOC-amino acid in the required sequence until the desired BOC-hexapeptide-O-CH$_2$ φ-resin was obtained.

DCCI was used as the sole coupling agent in every step.

The coupling of each amino acid proceeded smoothly. Best yields were obtained when the coupling was repeated in each step. When the coupling was repeated, the initial two chloroform washes, the deblocking step and the succeeding three chloroform washes were all omitted and replaced by a single chloroform wash.

The coupling reactions were carried out in methylene chloride, freshly degassed DMF or a mixture of these two solvents. The N-terminal amino group was blocked with a BOC group in each case; the hydroxy group of Thr was blocked with Bzl and the ε-amino group of Lys with 2-Cl-CBZ.

When the desired BOC-hexapeptide-O-CH$_2$ φ-resin was obtained, the N-terminal BOC group was removed by the terminal deblocking procedure set forth in Table V.

TABLE III

| Solvent or reagent (number of treatments or washes) | CH$_2$Cl$_2$ (2) | 25% TFA in CH$_2$Cl$_2$ (2) | CH$_2$Cl$_2$ (3) | NEt$_3$—CH$_2$Cl$_2$ (1:9) (2) | CHCl$_3$ (3) CH$_2$Cl$_2$ (3) | BOC AA in CH$_2$Cl$_2$ DMF or a mixture of both | 0.5 M DCCI in CH$_2$Cl$_2$ | DMF (1) MeOH DMF (1) MeOH (1) CH$_2$Cl$_2$ |
|---|---|---|---|---|---|---|---|---|
| Vol. in ml. | 40 | 20 | 40 | 40 | 40 | 25 | 10 | 40 |
| Time in min. | 5 | 2 and 25 | 2 | 5 and 5 | 2 | 2 | 5 coupling 30 | 2 |

TABLE IV

| Protected Amino Acid | Solvent Ml. |
|---|---|
| BOC—(2-Cl—CBZ)Lys (2.24 g) Recouple | 25 ml CH$_2$Cl$_2$ |
| BOC—D-Trp (1.52 g) Recouple | 20 ml CH$_2$Cl$_2$, 5 ml DMF |
| BOC—Phe (1.32 g) Recouple | 25 ml CH$_2$Cl$_2$ |
| BOC—Pro(γ-t-OH) (1.80 g) Recouple | 25 ml CH$_2$Cl$_2$ |
| BOC—Phe (1.32 g) | 25 ml CH$_2$Cl$_2$ |

TABLE V
TERMINAL DEBLOCKING PROGRAM

| Solvent or reagent (number of treatments or washes) | CH$_2$Cl$_2$ (1) | 25% TFA in CH$_2$Cl$_2$ + 1% Ethanedithiol (2) | CH$_2$Cl$_2$ (3) | MeOH (2) CH$_2$Cl$_2$ (1) MeOH (2) CH$_2$Cl$_2$ (2) |
|---|---|---|---|---|
| Vol. in ml. | 40 | 40 | 40 | 40 |
| Time in minutes | 5 | 2 and 25 | 2 | 2 |

After the procedures of Tables III, IV and V were completed, the blocked hexapeptide-OCH$_2$φ-resin is dried overnight and weighs 3.5 g.

EXAMPLE 2

Preparation of
Phe-Pro-(γ-t-OH)Phe-D-Trp-Lys(ε-2-Cl-CBZ)-
Thr(BZL)-NHNH$_2$

The resin from Example 1 is combined with 30 ml. of a 2:1 mixture of methanol and hydrazine and stirred at room temperature for 0.5 hours. The insoluble resin is removed by filtration and the solution is evaporated to remove the methanol and hydrazine. The residue is triturated with water, filtered and placed under high vacuum overnight to remove all volatile materials. A foam resulted from dissolving the residue in methanol, filtering and evaporating to dryness, weighing 2.0 g.

EXAMPLE 3

Preparation of
Phe-Pro-(γ-t-OH)Phe-D-Trp-Lys(ε2-Cl-CBZ)-
Thr(BZL)-N$_3$

The solid from Example 2 is combined with 15 ml. of degassed dimethylformamide under a blanket of nitrogen and cooled to −10° C., and 5 equivalents of 5.8 M. hydrogen chloride in tetrahydrofuran (1.7 ml.) is added. The solution is cooled to −25° C. and 5 ml. of a 1:19 mixture of isoamyl nitrite in dimethylformamide is added. The completion of the reaction is followed by thin layer chromatography and the disappearance of the hydrazide starting material.

EXAMPLE 4

Preparation of
Cyclo(Phe-Pro-(γ-t-OH)Phe-D-Trp-Lys-(ε-2-Cl-CBZ)-
Thr(BZL)

The azide compound of Example 3 is added to 600 ml. of degassed dimethylformamide, precooled to −25° C., the pH adjusted to 8, and the reaction mixture placed in the freezer overnight. The pH is readjusted to 8 if necessary after about 14 hours and the mixture stored for 16 hours at −20° C. and 16 hours at 5° C. Thin layer chromatography indicates that the reaction is completed. The mixture is concentrated to dryness dissolved in 150 ml. of a 3:1 dimethylformamide/water mixture and treated with a mixed bed anion-cation exchange resin for 2 hours. The mixture is filtered and concentrated to dryness in vacuo, and the residue is triturated with water to give 2.1 g of product. This product was purified by silica gel chromatography using chloroform-methanol 96:4 for elution of the product. Combination of fractions with pure product afforded 1.67 g of product.

EXAMPLE 5

Preparation of
Cyclo(D-Trp-Lys-Thr-Phe-Pro-(γ-t-OH)-Phe)

2.13 G. (2 mmoles) of the protected cyclic hexapeptide of Example 4 is combined in a teflon lined chamber with 2 ml. of anisole. The chamber is then evacuated and filled with liquid hydrogen fluoride at the temperature of the dry ice/acetone bath. The temperature is raised to 0° C. and stirring continued for 1 hour. The hydrogen fluoride is allowed to evaporate and the residue placed in vacuo until a slurry is formed. The slurry is treated with ethyl acetate and filtered affording 1.19 g. of a fine powder. 360 Mg. of this powder was purified by chromatography on Sephadex G-25-F using 2N acetic acid as eluent and by silica gel using the solvent mixture chloroform-methanol-concentrated ammonium hydroxide 80:20:2 as eluent. Fractions containing pure product were evaporated and lyophilized from dilute acetic acid to give 0.18 g of product.

EXAMPLE 6

Cyclo[Phe-Pro(γ-t-OAC)-Phe-D-Trp-Lys(2-Cl-CBZ)-
Thr-(BZl)]

To a solution of cyclo [Phe-Pro(γ-t-OH)-Phe-D-Trp-Lys(2-Cl-CBZ)-Thr(BZl)] (299 mg) in 4 ml CH$_2$Cl$_2$ was added 120 mg dimethylaminopyridine (DMAP) and 0.5 ml acetic anhydride. After 1 hour at 25° C., 10 ml of CH$_2$Cl$_2$ was added and the solution was extracted with 2 portions of 10% sodium bicarbonate. The organic layer was dried with anhydrous magnesium sulfate, filtered, and the solvent was evaporated. The residue was triturated with cold water and dried over potassium hydroxide to give 282 mg of cyclo[Phe-Pro(γ-t-OAC)-Phe-D-Trp-Lys(2-Cl-CBZ)-Thr-(BZl)]. Product was 90% pure as measured by HPLC.

To a mixture of the product of Example 6 (255 mg) and anisole (1 ml) was added at −40° C. 10–15 ml HF and the solution was kept at −10° C. for 25 minutes. HF was evaporated in vacuo and the residue triturated with ethyl acetate-petroleum ether (4:1).

The solid was filtered and dried in vacuo over potassium hydroxide pellets to give 0.17 g of crude product. Chromatography on silica gel 60 (230–400 mesh) (35 g) using the solvent mixture chloroform, methanol, concentrated ammonium hydroxide (80–20–2) for elution resulted in isolation of pure product (77 mg) and product containing minor impurities (46 mg). Product was 97% pure as measured by HPLC and exhibited R$_f$s of 0.25 and 0.45 in chloroform, methanol, concentrated ammonium hydroxide (80–20–2 and 70–30–3 respectively).

EXAMPLE 7

Cyclo
[Phe-Pro(γ-t-OTs)-Phe-D-Trp-Lys-(2-Cl-CBZ)-Thr-(BZl)]

A mixture of cyclo[Phe-Pro(γ-t-OH)-Phe-D-Trp-Lys(2-Cl-CBZ)-Thr(BZl)] (507 mg), dimethylamino pyridine (153 mg), and tosylchloride (146 mg) in methylene chloride (3 ml) was kept at 25° C. for 20 hours. Methylene chloride (20 ml) was added and the solution was extracted with aqueous sodium bicarbonate (1x) and the organic layer was dried with anhydrous magnesium sulfate. Evaporation of solvent gave 0.63 g crude product which was chromatographed using 150 g silica gel 60 (230–400 mesh) and the solvent mixture chloroform-isopropanol (95–5). Combining fractions which contained product having an R$_f$ of 0.45 (95–5) gave 370 mg of product (98% pure by HPLC) and 150 mg of product from side fractions.

EXAMPLE 8

Cyclo
[Phe-Pro(γ-cis-OAc)-Phe-D-Trp-Lys(2-Cl-CBZ)-Thr (BZl)]

A solution of the product of Example 7 (360 mg) and Cesium acetate (375 mg) in 2.5 ml N,N-dimethylformamide was kept at 50° C. for 7 hours. The solvent was evaporated in vacuo and the residue was triturated with cold water to give 329 mg of product. Tlc showed product to be somewhat more polar than the trans isomer as measured by Tlc in CHCl₃-i-PrOH.

EXAMPLE 9

Cyclo(Phe-Pro(γ-cis-OAc)-Phe-D-Trp-Lys-Thr) and Cyclo(Phe-Pro(γ-cis-OH)-Phe-D-Trp-Lys-Thr)

The blocked product of Example 8 was treated with HF as previously described using 1.2 ml of anisole and 10-15 ml of HF. The crude product was a mixture of the cis hydroxy and cis-acetoxy ($R_f$ 0.25 and 0.45, CHCl₃-MeOH concentrated NH₄OH; 70-30-3) compounds which was separated by chromatography using silica gel 60 (230–400-mesh) and chloroform-methanol-concentrated ammonium hydroxide (75-25-2.5). The cis-acetoxy products (120 mg) and the cis hydroxy product (30 mg) were isolated having purity of 90% and 94% as measured by HPLC.

Following the above procedure, and by modifying only the selection and order of amino acids in the process of Example 1, there are prepared other cyclic hexapeptides of this invention, such as Cyclo(Phe-Pro(γ-t-OH)Phe-Trp-Lys-Thr).

Analogs of somatostatin were compared to somatostatin in their ability to decrease the levels of portal vein glucagon and insulin in anesthetized rats. Male Sprague-Dawley rats (Charles River CD) weighing 160-200 g were anestetized with urethane (150 mg/100 g of body weight; Aldrich). Saline or peptides were administered via the external jugular vein. After 5 minutes, the portal vein was exposed, and blood was collected via syringe containing 3 mg of EDTA and placed in chilled tubes containing 100 μl of Trasylol (FBA Pharmaceuticals) for subsequent hormone analysis. Plasma levels of glucagon were determined by the method of Faloona and Unger, *Methods of Hormone Radioimmunossay*, Jaffe and Behrman (Eds), Academic Press, New York, Vol. II, pp. 257-527 (1976), utilizing glucagon antisera 30K obtained from R. Unger (Dallas, TX). Plasma levels of insulin were determined by a modification of the procedure of Herbert et al., *J. Clin. Endocrinol. Metab.*, 25, 1375-1384 (1965).

The test results for some of the compounds of this invention are recorded below with the results for somatostatin listed first and given the arbitrary value of 1. The results for the instant compounds are given as multiples or fractions of the effect of somatostatin. The first of the instant compounds listed is the compound prepared in Example 1-5. The compound is written slightly different, however, to conform to the order of the amino acids found in somatostatin.

| Activity of Cyclichexapeptide Analogs of Somatostatin | | |
|---|---|---|
| Compound | Insulin Release Inhibition | Glucagon Inhibition |
| Somatostatin | 1 | 1 |
| Cyclo(Pro(γ-t-OH)—Phe—D-Trp—Lys—Thr—Phe) | 18 | 15 |
| Cyclo(Pro(γ-t-OH)—Phe—Trp—Lys—Thr—Phe) | 5.6 | 6 |
| Cyclo(Pro(γ-t-OAc)—Phe D-Trp—Lys—Thr—Phe) | 10 | 20 |
| Cyclo(Pro(γ-cis-OH)—Phe—D-Trp—Lys—Thr—Phe) | 68 | 71 |
| Cyclo(Pro—(γ-cis-OAc)—Phe D-Trp—Lys—Thr—Phe) | 95 | 84 |

What is claimed is:
1. A compound having the formula:

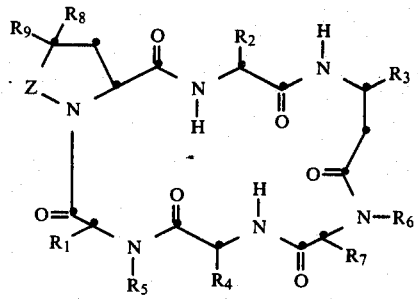

wherein
Z is $(CH_2)_n$ and n is 1 or 2;
$R_1$ and $R_2$ are independently lower alkyl, benzyl, naphthylmethyl, indolylmethyl, substituted benzyl wherein the substituent may be one or two of loweralkyl, halogen, hydroxy, amino, nitro or loweralkoxy; and loweralkyl substituted with a 5- or 6-membered heterocyclic ring;
$R_3$ is 3-indolylmethyl, naphthylmethyl, or substituted 3-indolylmethyl wherein the substituent may be loweralkyl, loweralkoxy or halogen;
$R_4$ is loweralkyl, hydroxyloweralkyl, benzyl, carboxyloweralkyl, aminoloweralkyl or substituted hydroxy benzyl wherein the substituent may be loweralkyl, loweralkoxy, hydroxy, halogen, amino or nitro;
$R_5$ and $R_6$ are independently hydrogen or methyl;
$R_7$ is aminocyclohexylmethyl, aminomethybenzyl or

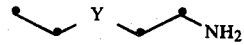

wherein Y is $(CH_2)_m$ and m is 0, 1 or 2 or sulfur such that the sulfur may be in any position along the chain;
$R_8$ and $R_9$ are independently hydrogen, loweralkyl, heteroalkyl wherein the heteroatom is oxygen, sulfur or nitrogen, hydroxy, and alkanoyl, up to 20 carbon atoms, derivatives of the hydroxy mercapto and amino groups, mercapto and amino, provided that $R_8$ and $R_9$ are not simultaneously hydrogen.

2. A compound of claim 1 wherein Z is $CH_2$ and n is 1 or 2;
$R_1$ and $R_2$ are as defined in claim 1;
$R_3$ is 3-indolylmethyl or substituted indolylmethyl wherein the substituent is methoxy or fluoro;
$R_4$ is methyl, ethyl, hydroxymethyl or hydroxyethyl; and
$R_5$ and $R_6$ are hydrogen;
$R_7$ is $CH_2CH_2$—$CH_2CH_2NH_2$;
$R_8$ is hydrogen; and
$R_9$ is hydroxy or acetoxy.

3. A compound of claim 2 wherein Z is $CH_2$ and n is 1;
$R_3$ is 3-indolylmethyl;
$R_4$ is hydroxyethyl;
$R_5$ and $R_6$ are hydrogen;
$R_8$ is hydrogen; and
$R_9$ is hydroxy or acetoxy.

4. The compound of claim 2 which is cyclo (Pro(γ-cis-OH)-Tyr-D-Trp-Lys-Val-Phe).

5. The compound of claim 2 which is cyclo (Pro(γ-t-OH)-Phe-D-Trp-Lys-Thr-Phe).

6. The compound of claim 2 which is cyclo (Pro-(γ-t-OH)-Phe-L-Trp-Lys-Thr-Phe).

7. The compound of claim 2 which is cyclo (Pro(γ-t-OAc)-Phe-D-Trp-Lys-Thr-Phe).

8. The compound of claim 2 which is cyclo (Pro(γ-cis-OH)-Phe-D-Trp-Lys-Thr-Phe).

9. The compound of claim 2 which is cyclo (Pro(γ-cis-OAc)-Phe-D-Trp-Lys-Thr-Phe).

10. The compound of claim 2 which is cyclo (Pro(γ-cis-OH)-Phe-L-Trp-Lys-Thr-Phe).

11. The compound of claim 2 which is cyclo (Pro(γ-cis-OAc)-Phe-Trp-Lys-Thr-Phe).

12. The compound of claim 2 which is cyclo (Pro(γ-t-OAc)-Phe-Trp-Lys-Thr-Phe).

* * * * *